July 2, 1940. J. DE VINK Plant Pat. 408
ROSE PLANT
Filed Feb. 27, 1940
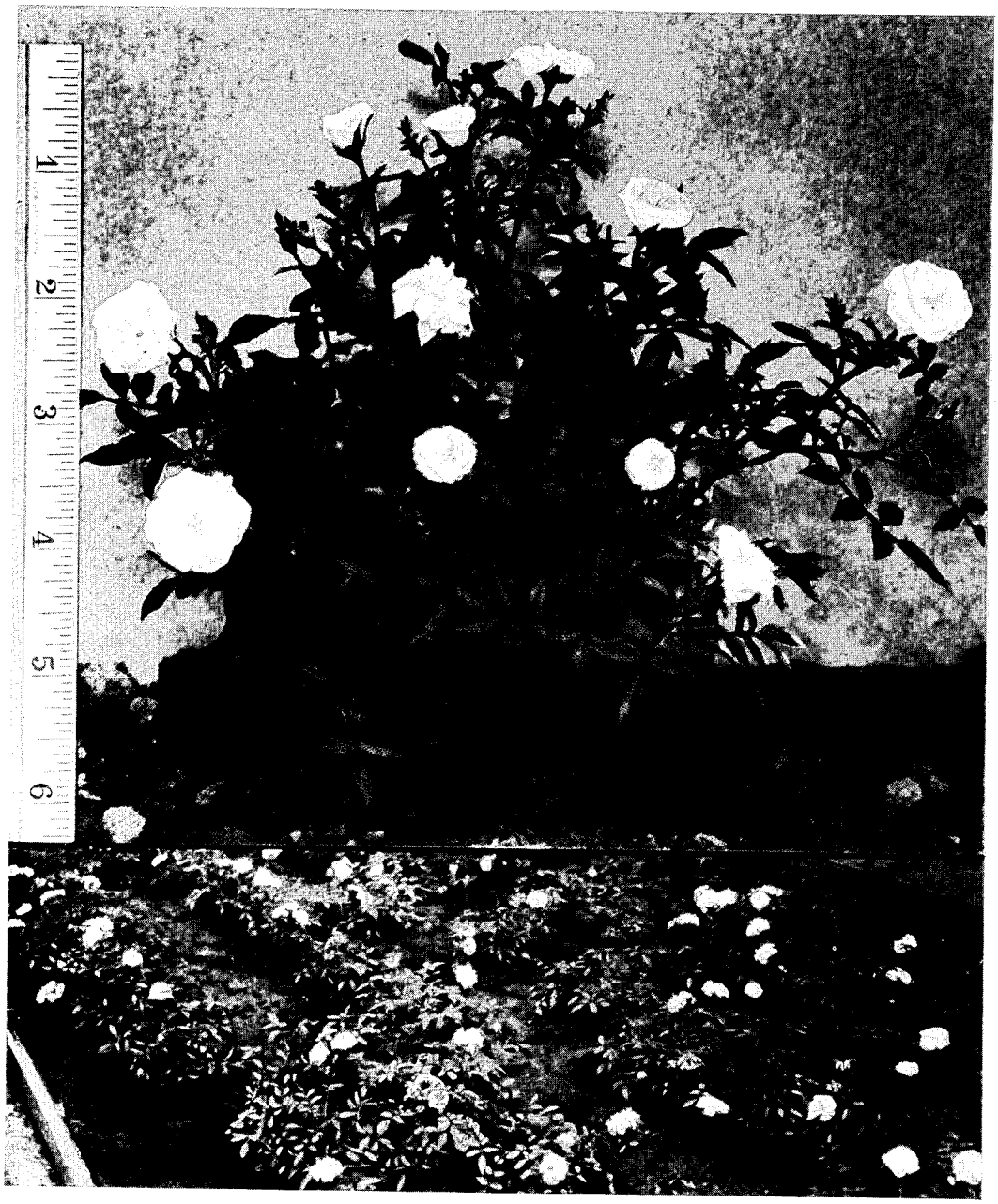
Inventor
John de Vink
By Robbins Robb
Attorneys Patented July 2, 1940

UNITED STATES PATENT OFFICE

408

ROSE PLANT

John de Vink, Boskoop, Netherlands, assignor to
The Conard-Pyle Company, West Grove, Pa.

Application February 27, 1940, Serial No. 321,109

1 Claim. (Cl. 47—61)

The present invention relates to a new and distinct variety of rose plant of the miniature type, the result of a cross between my prior dwarf origination Tom Thumb (Plant Patent No. 169) and the highly valued Polyantha Ellen Poulsen.

In my extensive work in the field of miniature roses having the Lawranceana background, I have found none having as great attractiveness with respect to the form of the bud and flower, and the color thereof has not even been approached by any flower of the small rose type. In addition to the foregoing distinctions, the size of the plant, small size and artistic arrangement of the leaflet and the large number of petals for so small a flower present novel features which make this variety entirely unique in the closs of dwarf roses.

In the drawing, I have illustrated in color a full size plant associated with a rule to show the actual size thereof and also a section of a garden planting of these roses to show their display characteristics.

A sexual reproduction shows that the variety holds its distinguishing characteristics through succeeding propagations.

The following is a detailed description of this new rose, the color terminology employed therein being in accord with Ridgway's Color Standard.

Type: Hardy; dwarf; greenhouse and outdoors; seedling; for cut flowers and garden decoration.

Class: Miniature (*chinensis* minima×Polyantha).

Parentage:

*Seed parent.*—Ellen Poulsen.

*Pollen parent.*—Tom Thumb.

*Flower*

Locality where grown: West Grove, Pennsylvania.

Flowers borne: Singly and several to stem; in irregular clusters, on normal short to medium stems.

Quantity of bloom: Free, outdoors and in greenhouse.

Continuity: Continuous.

Fragrance: Slight; centifolia.

Bud:

*Peduncle.*—Medium length; slender; erect; Yellowish Oil Green, Plate V; entirely smooth.

*Before calyx breaks.—Size*—small. *Form*—ovoid with a conspicuous neck, with foliaceous appendages on the surface of the bud; with slender foliaceous parts extending beyond the tip of the bud equal to one-half or more of its length.

*As calyx breaks.—Color:* in warm weather—White; in cool weather—Hermosa Pink, Plate I.

*As first petal opens.—Size*—very small. *Form*—very short, globular. *Color*—outside: in warm weather—White; in cool weather—Hermosa Pink. Inside: in warm weather—White with faint Hermosa Pink center; in cool weather—Hermosa Pink. *Opening*—opens up well.

Bloom:

*Size.*—Small, ¾ inch to 1⅛ inches.

*Petalage.*—Very double (usually with no stamens showing), from 50 to 60 petals; arranged regularly.

*Form.*—Very full, globular at first; becoming flat; petals remaining at first tightly cupped, rolled outward; becoming later, at maturity, loosely flat.

Petals: Soft, with inside and outside satiny.

*Shape.*—Outside—round; apex flat, with one notch. Intermediate—round, scalloped with apex flat with one notch. Inside—round, scalloped with apex flat with one notch.

This description of a newly opened flower was made from a rose grown in a greenhouse, in November, 1939, at West Grove, Pennsylvania:

*Color.*—outside petal: Outside surface—White faintly tinted with Hermosa Pink, Plate I; inside surface—White. Intermediate petal: outside surface—White; inside surface—White. Inner petal: outside surface—Faint Hermosa Pink, Plate I; inside surface—Faint Hermosa Pink, Plate I.

This description was made from a rose that was open for three days in a greenhouse, in November, 1939, at West Grove, Pennsylvania:

*Color.*—outside petal: outside surface—Hermosa Pink, Plate I with White base; inside surface—Faint Hermosa Pink. Inside petal: outside surface—Faint Hermosa Pink. Inside surface—Faint Hermosa Pink.

*General color effect.*—Newly opened flower—White in warm weather; Hermosa Pink in cool weather. Three days open—White in warm weather; Hermosa Pink in cool weather.

*Behavior.*—Persist; fading brown; affected by cold weather—color gets Hermosa to Faint Hermosa Pink, Plate I.

*Flower longevity.*—Cut roses grown in greenhouse kept at living room temperatures 6 to 7 days in November.

*Reproductive organs*

Stamens: Very few, mixed with petaloids.

Filaments: Medium length; Pale Orange Yellow, Plate III; few with anthers.

Anthers: Small; Pale Orange Yellow, Plate III.
Pollen: None showing.
Pistils: Few.
Styles: Uneven; short; thin; bunched.
Stigma: White.
Ovaries: All enclosed in calyx.
Hips: No record.

*Plant*

Foliage:

*Leaves.*—Compound of 3, 5, 7; abundant; very small; thin; wrinkled.

*Leaflets.*—Lanceolate with apex acute, base obtuse, margin simply serrate.

*Color.* — *Mature:* upper surface — Cedar Green, Plate VI; under surface—Spinach Green, Plate V. *Young:* upper surface—Cedar Green, Plate VI; under surface—Parrot Green, Plate VI.

*Rachis.*—(The supporting stem of the compound leaf), medium heavy. Upper side—grooved, hairy; under side—sparsely prickly.

*Stipules.*—Medium length, narrow, medium width with medium points, turning out at an angle less than 90°.

*Disease.*—Resistant to blackspot.

Growth:

*Habit.*—Dwarf, bushy, much branched.

*Growth.*—Moderate.

*Canes.*—Lightweight.

*Main stems.*—Spinach Green, Plate V. *Thorns*—several, long, straight with short narrow base. *Prickles* — none. *Hairs* — none.

*Branches.* — Spinach Green, Plate V. *Thorns*—few, straight with narrow base. *Prickles*—none. *Hairs*—none.

*New shoots.* — Dull Bay Brown, Plate II, *Thorns*—several, long, straight with narrow base. *Prickles*—none. *Hairs*—none.

I claim:

A new and distinct variety of miniature rose plant characterized as to novelty by its dwarf size, the small size and arrangement of the leaflets, the form and color of the bud and flower, and the large number of petals thereof, substantially as shown and described.

JOHN DE VINK.